United States Patent [19]

Meyer et al.

[11] 4,360,520
[45] Nov. 23, 1982

[54] 1,4-DIHYDROPYRIDAZINE COMPOUNDS, AND THEIR MEDICINAL USE

[75] Inventors: Horst Meyer; Gerhard Franckowiak; Friedrich Bossert; Arend Heise; Stanislav Kazda; Kurt Stoepel; Robertson Towart, all of Wuppertal; Egbert Wehinger, Velbert, all of Fed. Rep. of Germany

[73] Assignee: Bayer Aktiengesellschaft, Leverkusen, Fed. Rep. of Germany

[21] Appl. No.: 941,527

[22] Filed: Sep. 11, 1978

[30] Foreign Application Priority Data

Sep. 14, 1977 [DE] Fed. Rep. of Germany ....... 2741260

[51] Int. Cl.³ .................. A61K 31/495; C07D 237/04

[52] U.S. Cl. .................................... 424/250; 424/251; 260/243.3; 544/224; 544/238

[58] Field of Search ................. 544/238, 224; 424/250

[56] References Cited

U.S. PATENT DOCUMENTS 4,011,212 3/1977 Baldwin et al. ..................... 544/238
4,058,390 11/1977 Schönbeck et al. ................ 544/238

Primary Examiner—Donald G. Daus
Assistant Examiner—James H. Turnipseed

[57] ABSTRACT

The invention includes new 1,4-dihydropyridazine compounds, compositions containing said 1,4-dihydropyridazine compounds and methods for the use of said compounds and compositions. Also included in the invention are methods for preparing the new 1,4-dihydropyridazine compounds.

13 Claims, No Drawings

1,4-DIHYDROPYRIDAZINE COMPOUNDS, AND THEIR MEDICINAL USE

The present invention relates to certain new 1,4-dihydropyridazine compounds, a process for their production and to their use as medicaments, in particular as agents having an influence on the circulation and spasmolytic agents.

It has already been disclosed that 1,4-dihydropyridazines are obtained when substituted 1,4-dicarbonyl compounds are reacted with hydrazine hydrate (compare W. Borsche and M. Spannagel, Liebigs Ann. Chem. 331, 300 et seq. (1904)).

The present invention relates to compounds which are 1,4-dihydropyridazines of the following general formula I

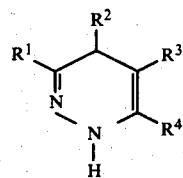
(I)

in which $R^1$ is hydrogen or a straight-chain, branched or cyclic, saturated or unsaturated, aliphatic hydrocarbon radical which is optionally interrupted in the chain by one or two oxygen or sulphur atoms, and/or which is optionally substituted by hydroxyl or halogen, or by a phenoxy or phenyl group which is optionally substituted by halogen, cyano, amino, alkylamino, alkoxy, alkyl, trifluoromethyl, trifluoromethoxy or nitro, or by an $\alpha$-, $\beta$- or $\gamma$-pyridyl group, or by an amino group optionally substituted by one substituent or two identical or different substituents each of which is alkyl, alkoxyalkyl, aryl and aralkyl, these substituents optionally forming a 5-membered to 7-membered ring with the nitrogen atom and optionally with a further heteroatom, or is aryl, or hetero-aryl which is thienyl, furyl, pyrryl, pyrazolyl, imidazolyl, oxazolyl, isoxazolyl, thiazolyl,pyridyl, pyridazinyl, pyrimidyl, pyrazinyl, quinolyl, isoquinolyl, indolyl, benzimidazolyl, quinazolyl or quinoxalyl, the aryl radical and the hetero-aryl radical optionally containing from 1 to 3 identical or different substituents each of which is phenyl, alkyl, alkenyl, alkinyl, alkoxy, alkenoxy, alkinoxy, alkylene, dioxyalkylene, halogen, trifluoromethyl, trifluoromethoxy, hydroxyl, amino, alkylamino, nitro, cyano, azido, carboxyl, carbalkoxy, carboxamido, sulphonamido, $SO_m$-alkyl or $SO_m$-trifluoroalkyl (m=0 to 2), $R^2$ is aryl, or hetero-aryl and is thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl, the aryl and the hetero-aryl optionally containing from 1 to 3 identical or different substituents each of which is phenyl, alkyl, alkenyl, alkinyl, alkoxy, alkenoxy, alkinoxy, alkylene, dioxyalkylene, halogen, trifluoromethyl, trifluoromethoxy, hydroxyl, amino, alkylamino, nitro, cyano, azido, carboxyl, carbalkoxy, carboxamido, sulphonamido, $SO_m$-alkyl or $SO_m$-trifluoroalkyl (m=0 to 2), the alkyl and alkoxy substituents in turn being optionally substituted by alkoxy, halogen, carboxyl, carbalkoxy, amino or alkylamino, $R^3$ is hydrogen, or represents the groups $COR^5$, wherein $R^5$ is alkyl, aryl, or aralkyl, amino or hydrazino optionally substituted by alkyl, aryl or aralkyl, or $R^5$ is a group $OR^6$, wherein $R^6$ is a straight-chain, branched or cyclic, saturated or unsaturated, aliphatic hydrocarbon radical which is optionally interrupted in the chain by 1 or 2 oxygen or sulphur atoms, and/or which is optionally substituted by hydroxyl or halogen, or by a phenoxy or phenyl group which is optionally substituted by halogen, cyano, amino, alkylamino, alkoxy, alkyl, trifluoromethyl or nitro, or by an $\alpha$-, $\beta$- or $\gamma$-pyridyl group, or by an amino group optionally substituted by one substituent or two identical or different substituents each of which is alkyl, alkoxyalkyl, aryl and aralkyl, these substituents optionally forming a 5-membered to 7-membered ring with the nitrogen atom, and optionally with oxygen, sulphur or nitrogen atom as a further heteroatom, or $R^6$ is aryl optionally substituted by one or two identical or different substituents each of which is alkyl, alkoxy, aryl, aralkyl, halogen, nitro, cyano, trifluoromethyl, trifluoromethoxy, amino, monoalkylamino or dialkylamino, and $R^4$ is hydrogen or straight-chain or branched alkyl optionally substituted by hydroxyl, halogen, acyloxy, amino, dialkylamino or aminoacyl, or is perfluoroalkyl or aryl, aralkyl or thienyl, furyl, pyrryl or pyridyl optionally having from 1 to 3 identical or different substituents, or $R^4$ and $R^5$ together with the carbon atom to which $R^5$ is bonded and the carbon atoms to which $R^3$ and $R^4$ are bonded, and optionally with oxygen, nitrogen or sulphur as a hetero-atom, represent a 5-membered to 7-membered ring. In the definitions of $R^1$, $R^2$, $R^3$, $R^4$, $R^5$ and $R^6$, alkyl substituents and the alkyl portions of substituents having an alkyl portion preferably contain up to 12 carbon atoms in said alkyl moiety; also aryl is preferably phenyl and naphthyl; and cyclic aliphatic hydrocarbon radicals contain 3 to 8, preferably 5 to 6 ring members.

It has been found that a compound of the invention may be obtained by a process in which a 1,4-dicarbonyl compound of the general formula II

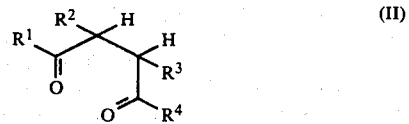
(II)

in which $R^1$, $R^2$, $R^3$ and $R^4$ have the same meaning as defined hereinbefore in formula I, is reacted with hydrazine of the formula III $$H_2N-NH_2 \qquad (III)$$

in an organic solvent.

The new 1,4-dihydropyridazine compounds according to the invention have valuable pharmacological properties. Because of their circulation-influencing and spasmolytic actions, they can be used as anti-hypertensive agents, as vasodilators and as coronary therapeutic agents and spasmolytic agents. No therapeutic actions, and especially no actions on the circulation, have been disclosed for the dihydropyridazines known hitherto. The compounds according to the invention thus represent a novel class of substances for the treatment of the circulation and for the treatment of diseases of the gastro-intestinal tract, the urogenital tract and the respiratory system.

If 2-acetyl-3-(2'-nitrophenyl)-4-oxo-hexanoic acid ethyl ester and hydrazine are used as starting materials, the course of the reaction can be represented by the following reaction equation by way of example:

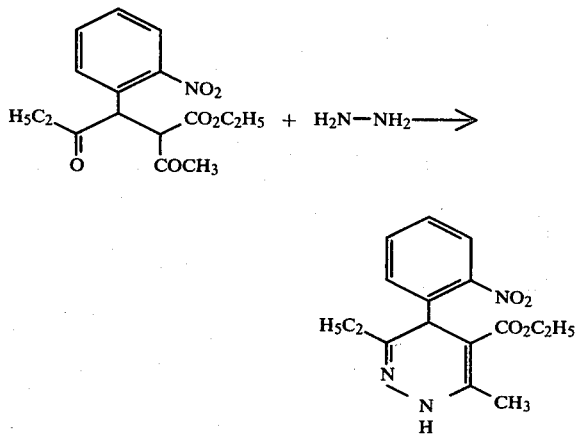

According to the procedure indicated, a 1,4-dicarbonyl compound of the formula II is reacted with hydrazine of the formula III to give a 1,4-dihydropyridazine derivative of the formula I

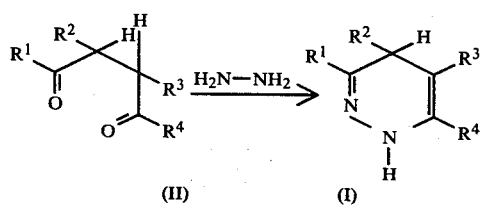

Preferably, in the formulae I and II, $R^1$ is hydrogen, or straight-chain, branched or cyclic, saturated or unsaturated, aliphatic hydrocarbon having up to 8, in particular up to 6, carbon atoms, optionally interrupted in the chain by 1 oxygen and/or sulphur atom, and/or optionally substituted by hydroxyl or by halogen, in particular fluorine, or by a phenoxy or phenyl group which is optionally substituted by halogen, in particular fluorine, chlorine or bromine, cyano, amino, alkylamino or dialkylamino with, in each case, 1 or 2 carbon atoms per alkyl group, alkoxy having from 1 to 4 carbon atoms, alkyl having from 1 to 4 carbon atoms, trifluoromethyl, trifluoromethoxy or nitro, or by an α-, β- or γ-pyridyl group, or by an amino group which carries two identical or different substituents each of which is hydrogen, alkyl having from 1 to 4 carbon atoms, alkoxyalkyl having up to 6, in particular up to 4, carbon atoms, phenyl or aralkyl, in particular benzyl, or these substituents optionally representing, together with the nitrogen atom and optionally oxygen or sulphur atom as a further hetero-atom, a 5-membered to 7-membered ring, or represents a phenyl or naphthyl radical, or represents a thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl radical, the aryl and hetero-aryl radicals mentioned, in particular the phenyl radical, optionally containing 1 to 2, identical or different substituents, preferred substituents which may be mentioned being phenyl, straight-chain or branched alkyl having from 1 to 8, in particular from 1 to 4, carbon atoms, cycloalkyl having from 3 to 7 carbon atoms, alkenyl or alkinyl having from 2 to 6 carbon atoms, in particular 2 to 3 carbon atoms, alkoxy having preferably from 1 to 4, in particular 1 to 2, carbon atoms, alkenoxy and alkinoxy having from 2 to 6, in particular from 3 to 5, carbon atoms, dioxymethylene, halogen, such as fluorine, chlorine, bromine or iodine, in particular fluorine, chlorine or bromine, trifluoromethyl, trifluoromethoxy, nitro, cyano, azido, hydroxyl, amino, monoalkylamino or dialkylamino having preferably from 1 to 4, in particular 1 or 2, carbon atoms per alkyl group, carboxyl, carbalkoxy having preferably from 2 to 4, in particular 2 or 3, carbon atoms, carboxamido, sulphonamido or $SO_m$-alkyl or trifluoromethyl, m denoting a number from 0 to 2 and alkyl preferably containing from 1 to 4, in particular 1 or 2, carbon atoms;

$R^2$ represents phenyl or naphthyl, or represents thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl, the above mentioned aryl radicals and hetero-cyclic radicals, in particular the phenyl radical, optionally containing 1 to 2 identical or different substituents, preferred substituents which may be mentioned being phenyl, straight-chain or branched alkyl having from 1 to 8, in particular from 1 to 4, carbon atoms, cycloalkyl having from 3 to 7 carbon atoms, alkenyl or alkinyl having from 2 to 6 carbon atoms, in particular 2 to 3 carbon atoms, alkoxy having preferably from 1 to 4, in particular 1 or 2, carbon atoms, alkenoxy and alkinoxy having from 2 to 6, in particular from 3 to 5, carbon atoms, dioxymethylene, halogen, such as fluorine, chlorine, bromine or iodine, in particular fluorine, chlorine or bromine, trifluoromethyl, trifluoromethoxy, nitro, cyano, azido, hydroxyl, amino, monoalkylamino and dialkylamino having preferably from 1 to 4, particular 1 to 2, carbon atoms per alkyl group, carboxyl, carbalkoxy having preferably from 2 to 4, in particular 2 or 3, carbonatoms, carboxamido, sulphonamido or $SO_m$-alkyl or $SO_m$-trifluoromethyl, m denoting a number from 0 to 2 and alkyl preferably containing from 1 to 4, in particular 1 or 2, carbon atoms, wherein $R^3$ is hydrogen or a group $COR^5$ wherein $R^5$ preferably is straight-chain or branched alkyl having from 1 to 4 carbon atoms, or $R^5$ and $R^4$ together with the carbon atom to which $R^5$ is bonded and the carbon atoms to which $R^3$ and $R^4$ are bonded and optionally with oxygen, sulphur or nitrogen atom as a hetero-atom, represent a 5-membered to 7-membered, preferably a 5-membered or 6-membered, ring or $R^5$ is phenyl, benzyl, a hydrazine radical, an amino group or a monoalkylamino or dialkylamino group having up to 4 carbon atoms per alkyl group, the alkyl groups optionally forming, with the nitrogen atom, a 5-membered to 7-membered ring which can contain an oxygen or sulphur atom as a further hetero-atom, or $R^5$ represents a group $OR^6$, wherein $R^6$ preferably is a straight-chain, branched or cyclic, saturated or unsaturated aliphatic hydrocarbon radical having up to 8, in particular up to 6, carbon atoms, which is optionally interrupted in the chain by one or two oxygen or sulphur atoms, and/or which is optionally substituted by hydroxyl or halogen, preferably one or more fluorine atoms, or by phenoxy or phenyl optionally substituted by halogen, such as fluorine, chlorine or bromine, cyano, amino, monoalkylamino or dialkylamino having, in each case, 1 to 2 carbon atoms in each alkyl, alkoxy having from 1 to 4 carbon atoms, alkyl having from 1 to 4 carbon atoms, trifluoromethyl or nitro, or by α-, β- or γ-pyridyl, or by amino optionally having one or two identical or different substituents each of which is alkyl having up to 4 carbon atoms, phenyl or aralkyl, in particular benzyl, these substituents optionally representing, together with the nitrogen atom, a 5-membered to 7-membered ring which can contain an oxygen, sulphur or nitrogen atom as a further hetero-atom, the additional nitrogen atom being optionally substituted by lower alkyl, or $R^6$ is aryl, in particular phenyl, optionally having 1 or 2 identical or different substituents, preferred substituents which may be mentioned being straight-chain or branched alkyl having from 1 to 4 carbon atoms, alkoxy having 1 or 2 carbon atoms, halogen, such as fluorine, chlorine or bromine, cyano, trifluoromethyl, trifluoromethoxy, nitro, amino or monoalkylamino or dialkylamino with, in each case, 1 or 2 carbon atoms per alkyl group; and $R^4$ is hydrogen, or straight-chain or branched alkyl having from 1 to 4, in particular 1 or 2, carbon atoms, a perfluoroalkyl radical having, in particular, 1 or 2 carbon atoms, phenyl optionally substituted by nitro, or methoxy, or aralkyl, in particular benzyl, or hetaryl in particular thienyl, furyl or pyridyl.

The 1,4-dicarbonyl compounds of the formula II used as starting materials are known from the literature in some cases, or they can be prepared by methods which are known from the literature (compare H. Stetter, Angew. Chem. 88, 695 et seq. (1976) and F. Boberg and A. Kieso, Liebigs Ann. Chem 626, 71 et seq. (1959)).

Examples which may be mentioned are: 2-acetyl-3-(2'-nitrophenyl)-4-oxo-hexanoic acid ethyl ester, 2-acetyl-3-(3'-nitrophenyl)-4-oxo-hexanoic acid methyl ester, 2-acetyl-3-(2'-nitrophenyl)-4-oxo-heptanoic acid ethyl ester, 3-(3'-chlorophenyl)-4-oxo-2-propionyl-pentanoic acid ethyl ester, 2-acetyl-3-(2'-nitrophenyl)-4-oxo-hexanoic acid isobutyl ester, 2-acetyl-3-(4'-dimethylaminophenyl)-4-oxo-hexanoic acid cyclopentyl ester, 2-acetyl-3-(2'-cyanophenyl)-4-oxo-nonanoic acid ethyl ester, 2-acetyl-3-(2'-cyanophenyl)-4-oxo-hexanoic acid n-hexyl ester, 2-acetyl-3-(3'-methylphenyl)-4-oxo-hexanoic acid cyclohexyl ester, 3-(3'-nitrophenyl)-4-oxo-2-propionyl-pentanoic acid methyl ester, 2-acetyl-4-oxo-3-(4'-trifluoromethoxyphenyl)-butyric acid methyl ester, 2-acetyl-3-(4'-isopropylphenyl)-4-oxo-heptanoic acid isopropyl ester, 2-benzoyl-3-(4'-cyanophenyl)-4-oxo-hexanoic acid methyl ester, 3-(3'-chlorophenyl)-2-(4'-nitrobenzyl)-4-oxo-hexanoic acid ethyl ester, 2-acetyl-3-(3'-nitrophenyl)-4-oxo-5,5,6,6,6-pentafluorohexanoic acid ethyl ester, 3-(4'-chlorophenyl)-4-oxo-2-trifluoroacetyl-hexanoic acid methyl ester, 2-acetyl-3-(3'-nitrophenyl)-4-oxo-6-phenyl-hexanic acid methyl ester, 2-acetyl-3-(5'-chloro-2'-nitrophenyl)-4-oxo-hexanoic acid β-methoxyethyl ester, 2-acetyl-3-(3'-nitrophenyl)-4-oxo-hexanoic acid β-phenoxyethyl ester, 2-acetyl-3-(3'-methyl-mercaptophenyl)-4-oxo-pentanoic acid n-propyl ester, 2-acetyl-3-(2'-chloro-5'-nitrophenyl)-4-oxo-hexanoic acid isopropyl ester, 2-acetyl-3-(3',4'-dichlorophenyl)-4-oxo-hexanoic acid methyl ester, 2-acetoxy-acetyl-3-(3'-nitrophenyl)-4-oxo-hexanoic acid methyl ester, 2-acetyl-6-methoxy-4-oxo-3-(4'-trifluoromethylphenyl)-hexanoic acid t-butyl ester, 2-acetyl-3-(3'-cyanophenyl)-4-oxo-hexanoic acid β-methyl-mercaptoethyl ester, 2-acetyl-3-(3'-nitrophenyl)-4-oxo-hexanoic acid β-dimethylaminoethyl ester, 2-acetyl-4-oxo-3-(pyrid-3-yl)-hexanoic acid ethyl ester, 2-acetyl-3-(isoquinol-1-yl)-4-oxo-pentanoic acid methyl ester, 2-acetyl-3-(3'-chlorophenyl)-6-methylmercapto-4-oxo-hexanoic acid methyl ester, 2-acetyl-3-(4'-methylsulphonylphenyl)-4-oxo-hexanoic acid methyl ester, 2-acetyl-4-cyclohexyl-3-(2'-nitrophenyl)-4-oxo-butyric acid methyl ester, 4-oxo-3-(thien-2-yl)-2-trifluoroacetyl-hexanoic acid ethyl ester, 2-acetyl-4-oxo-3-(pyrr-3-yl)-hexanoic acid ethyl ester, 3-acetyl-4-(3'-nitrophenyl)-heptane-2,5-dione, 3-benzoyl-4-(4'-trifluoromethylphenyl)-heptane-2,5-dione, 2-[1'-(3'',4''-dichlorophenyl)-2'-oxo-butyl]-cyclohexane-1,3-dione, 2-[1'-(3''-nitrophenyl)-2'-oxo-propyl]-cyclohexane-1,3-dione, 2-[1'-(3''-nitrophenyl)-2'-oxo-2'-(pyrr-2-yl)-ethyl]-cyclohexane-1,3-dione, 2-acetyl-3-(3'-chlorophenyl)-4-oxo-4-(pyrr-2-yl)-butyric acid methyl ester, 2-acetyl-4-(4',4'-dimethyloxazolin-2-yl)-4-oxo-3-(2'-trifluoromethylphenyl)-butyric acid methyl ester, 2-acetyl-3,4-di-(pyrid-3-yl)-4-oxo-butyric acid methyl ester, 3-acetyl-2-(3'-chlorophenyl)-1-(fur-2-yl)-pentane-1,4-dione and 2-acetyl-3-(thiazol-5-yl)-4-oxo-hexanoic acid ethyl ester.

The 1,4-dicarbonyl compounds mentioned of the formula II can be employed as such or in the form of their corresponding 1-oxo-4-nitro derivatives. The corresponding 1,4-diketone can be prepared in situ from the nitro compounds with the aid of the Nef reaction. (Compare F. Boberg and G. R. Schultze, Chem. Ber. 90, 1215 et seq. (1957)).

The hydrazine used as a starting material is known from the literature (compare: L. F. Andrieth and B. A. Ogg, The Chemistry of Hydrazine, John Wiley and Sons Inc. New York N.Y. 1951) and may be used in any conventionally available form, such as, for example, hydrazine hydrate.

Suitable diluents are all the inert organic solvents. These include preferably, alcohols, particularly alkanols, such as ethanol, methanol and isopropanol, ethers, such as dioxane, diethyl ether, tetrahydrofurane, glycol monoethyl ether and glycol dimethyl ether, or glacial acetic acid, dimethylformamide, diethylformamide, dimethylsulphoxide, acetonitrile, pyridine and hexamethylphosphoric acid triamide.

The reaction temperature can be varied within a relatively wide range. In general, the reaction is carried out at from 20° C. to 150° C., preferably at from 40° to 120° C., and especially at the boiling point of the particular solvent.

The process can be carried out under normal pressure, but also under elevated pressure. In general, it is carried out under ambient pressure.

In carrying out the process according to the invention, 1 mol of the 1,4-dicarbonyl compound of the formula II is desirably reacted with one mol of the hydrazine compound of the formula III in a suitable solvent.

The isolation and purification of the compounds according to the invention is preferably carried out by distilling off the solvent in vacuo, if appropriate after separating off any insoluble substances, and recrystallising the residue, which in some cases is obtained in the crystalline form only after cooling with ice, from a suitable solvent.

The above preparation process is only mentioned for illustration, and the preparation of the compounds of the invention is not limited to this process, but any modification of this process can be applied in the same manner to the preparation of the compounds according to the invention.

Depending on the choice of starting substances, the compounds according to the invention can exist in stereoisomeric forms, which either behave as mirror images (enantiomers) or do not behave as mirror images (diastereomers). The present invention includes both the antipodes and the racemic forms as well as the diastereomer mixtures. The racemic forms can be separated in a known manner into the individual stereoisomers, as can the diastereomer mixtures (compare, for example, E. L. Eliel, Stereochemistry of Carbon Compounds, McGraw Hill, 1962).

Racemate mixtures can be separated into the pure racemates in a known manner on the basis of the physicochemical differences of the constituents, for example by chromatography and/or fractional crystallisation.

Pure racemates can be resolved according to known methods, for example by recrystallisation from an optically active solvent, with the aid of micro-organisms or by reaction with an optically active acid or base which forms salts with the racemic compound and separation of the salts obtained in this manner, for example on the basis of their different solubilities into the diastereomers from which the antipodes can be liberate by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end products in the form of the pure racemates or optical antipodes by employing starting substances, containin one or more asymmetrical C atoms, in the form of the pure racemates or optical antipodes.

In addition to the preparation examples listed below, the following active compounds according to the invention may be mentioned: 1,4-dihydro-3,6-dimethyl-4-(3'-nitrophenyl)-pyridazine-5-carboxylic acid ethyl ester, 3-ethyl-1,4-dihydro-6-methyl-4-(2'-nitrophenyl)-pyridazine-5-carboxylic acid isopropyl ester, 4-(2'-cyanophenyl)-1,4-dihydro-3,6-dimethyl-pyridazine-5-carboxylic acid ethyl ester, 6-ethyl-1,4-dihydro-3-methyl-4-(4'-trifluoromethylphenyl)-pyridazine-5-carboxylic acid methyl ester, 3-ethyl-1,4-dihydro-4-(4'-methoxyphenyl)-6-methyl-pyridazine-5-carboxylic acid ethyl ester, 1,4-dihydro-3,6-dimethyl-4-(2'-nitrophenyl)-pyridazine-5-carboxylic acid β-methoxyethyl ester, 3-ethyl-1,4-dihydro-6-methyl-4-(pyrid-2-yl)-pyridazine-5-carboxylic acid ethyl ester, 3-n-butyl-4-(3'-chlorophenyl)-1,4-dihydro-6-methyl-pyridazine-5-carboxylic acid t-butyl ester, 3-ethyl-1,4-dihydro-6-methyl-4-(4'-trifluoromethylmercapto)-pyridazine-5-carboxylic acid methyl ester, 1,4-dihydro-3,6-dimethyl-4-(2'-nitrophenyl)-pyridazine-5-carboxylic acid isopropyl ester, 1,4-dihydro-3,6-dimethyl-4-(3'-nitrophenyl)-pyridazine-5-carboxylic acid isopropyl ester, 3,6-diethyl-1,4-dihydro-4-(2'-nitrophenyl)-pyridazine-5-carboxylic acid n-propyl ester, 3-cyclohexyl-1,4-dihydro-6-methyl-4-(4'-trifluoromethylphenyl)-pyridazine-5-carboxylic acid t-butyl ester, 4-(3'-chlorophenyl)-1,4-dihydro-3-n-hexyl-6-methyl-pyridazine-5-carboxylic acid ethyl ester, 3-ethyl-1,4-dihydro-6-methyl-4-(2'-nitrophenyl)-pyridazine-5-carboxylic acid t-butyl ester, 3-ethyl-1,4-dihydro-6-methyl-4-(2'-nitrophenyl)-pyridazine-5-carboxylic acid β-methoxyethyl ester, 3-ethyl-1,4-dihydro-6-methyl-4-(3'-nitrophenyl)-pyridazine-5-carboxylic acid β-phenoxyethyl ester, 3-(β-n-butoxyethyl)-1,4-dihydro-6-methyl-4-(3'-nitrophenyl)-pyridazine-5-carboxylic acid ethyl ester, 3-ethyl-1,4-dihydro-6-methyl-4-(3'-nitrophenyl)-pyridazine-5-carboxylic acid β,β'-hexafluoroisopropyl ester, 3-ethyl-1,4-dihydro-4-(thien-2-yl)-6-trifluoromethyl-pyridazine-5-carboxylic acid ethyl ester, 3-(β-ethoxyethyl)-4-(3'-chlorophenyl)-1,4-dihydro-6-methyl-pyridazine-5-carboxylic acid methyl ester, 3-ethyl-1,4-dihydro-6-methyl-4-(pyrid-2-yl)-pyridazine-5-carboxylic acid β-dimethylaminoethyl ester, 3,6-diethyl-1,4-dihydro-4-(2'-trifluoromethylphenyl)-pyridazine-5-carboxylic acid ethyl ester, 1,4-dihydro-6-methyl-4-(3'-nitrophenyl)-pyridazine-5-carboxylic acid ethyl ester, 3-ethyl-1,4-dihydro-4-(3'-nitrophenyl)-6-phenyl-pyridazine-5-carboxylic acid methyl ester, 3-ethyl-1,4,5,6,7,8-hexahydro-5-oxo-4-(3'-nitrophenyl)-cinnoline, 1,4-dihydro-6-methyl-4-(3'-nitrophenyl)-3-pentafluoroethyl-pyridazine-5-carboxylic acid ethyl ester, 3-(β-(3'-chlorophenyl)-ethyl)-1,4-dihydro-6-methyl-4-(3'-nitrophenyl)-pyridazine-5-carboxylic acid methyl ester, 3-ethyl-4-(2'-cyanophenyl)-1,4-dihydro-6-methyl-pyridazine-5-carboxylic acid β-ethylmercaptoethyl ester, 1,4-dihydro-3-(fur-2-yl)-6-methyl-4-(2'-trifluoromethylphenyl)-pyridazine-5-carboxylic acid n-propyl ester, 3-ethyl-1,4-dihydro-4,6-di(pyrid-3-yl)-pyridazine, 3-(β-ethylmercaptoethyl)-1,4-dihydro-6-methyl-4-(2'-trifluoromethylphenyl)-pyridazine-5-carboxylic acid n-propyl ester, 3-ethyl-4-(3'-nitrophenyl)-5-oxo-1,4,5,7-tetrahydrofuro[4,3-c]pyridazine, 3-ethyl-6-acetoxymethyl-1,4-dihydro-4-(3'-nitrophenyl)-pyridazine-5-carboxylic acid ethyl ester, 1,4-dihydro-3,6-dimethyl-4-(isoquinol-1-yl)-pyridazine-5-carboxylic acid β-methoxyethyl ester, 3-ethyl-1,4-dihydro-6-methyl-4-(3'-methylsulphonylphenyl)-pyridazine-5-carboxylic acid ethyl ester, 5-acetyl-3-ethyl-4-(3'-chlorophenyl)-1,4-dihydro-6-methyl-pyridazine, 3-ethyl-5-benzoyl-4-(2'-cyanophenyl)-1,4-dihydro-6-methylpyridazine and 5-acetyl-3-n-butyl-1,4-dihydro-4-(3'-methylmercaptophenyl)-pyridazine.

Compounds of the formula I in which $R^1$ is hydrogen or straight-chain, branched or cyclic alkyl or alkenyl having up to 8, in particular up to 4, carbon atoms, the alkyl chain being optionally interrupted by an oxygen atom, or substituted by halogen, in particular fluorine, or by phenoxy, halogenophenyl, nitrophenyl, pyridyl, furyl, thienyl or dialkylamino or benzylalkylamino having 1 or 2 carbon atoms in the alkyl moiety in each case, or is pyridyl, furyl, thienyl or pyrryl, or is phenyl optionally substituted by one or two identical or different substituents each of which is halogen, nitro, cyano, trifluoromethyl, trifluoromethoxy or alkyl or alkoxy having in each case from 1 to 4, in particular 1 or 2, carbon atoms;

$R^2$ is phenyl optionally substituted by one or two identical or different substituents each of which is halogen, nitro, cyano, trifluoromethyl, trifluoromethoxy or alkyl, alkenyl, alkoxy or alkylmercapto having in each case from 1 to 4, in particular 1 or 2, carbon atoms, or is naphthyl, pyridyl, thienyl, pyrryl or furyl, $R^3$ is hydrogen or the group $COR^5$, wherein $R^5$ is hydrazino or an alkyl radical having from 1 to 4 carbon atoms or $R^5$ and $R^4$ together with the carbon atom to which $R^5$ is bonded and the carbon atoms to which $R^3$ and $R^4$ are bonded and optionally with a hetero-atom, such as oxygen, represent a 5-membered or 6-membered ring, or $R^5$ is a group $OR^6$, wherein $R^6$ is straight-chain, branched or cyclic alkyl, alkenyl or alkinyl having up to 6 carbon atoms, the alkyl and alkenyl group being optionally interrupted by an oxygen atom or the alkyl chain being optionally substituted by phenyl, phenoxy, halogenophenyl, nitrophenyl, pyridyl, dialkylamino with in each case 1 or 2 carbon atoms in the alkyl moiety, or benzyalkylamino having 1 or 2 carbon atoms in the alkyl moiety, and $R^4$ is alkyl having from 1 to 4, in particular 1 or 2, carbon atoms, or is phenyl, benzyl, pyridyl or thienyl, are particularly suitable as medicaments which influence the circulation and which have a spasmolytic action.

For the purpose of this specification the term "pharmaceutically acceptable bioprecursor" of an active compound of the invention means a compound having a structural formula different from the active compound but which nonetheless, upon administration to an animal, is converted in the patient's body to the active compound.

The new compounds have a broad and diverse spectrum of pharmacological action.

Specifically, the following principal actions could be demonstrated in animal experiments:

(1) On parenteral, oral and perlingual administration the compounds produce a distinct and long-lasting dilation of the coronary vessels. This action on the coronary vessels is intensified by a simultaneous nitrite-like effect of reducing the load on the heart. The compounds influence or modify the heart metabolism in the sense of an energy saving.

(2) The excitability of the stimulus formation and excitation conduction system within the heart is lowered, so that an antifibrillation action which can be demonstrated at therapeutic doses results.

(3) The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system).

(4) The compounds lower the blood pressure of normotonic and hypertonic animals and can thus be used an anti-hypertensive agents.

(5) The compounds have strongly muscular-spasmolytic actions which manifest themselves on the smooth muscle of the stomach, the intestinal tract, the urogenital tract and the respiratory system.

As stated above, the invention also relates to the use in medicine of the compounds of the invention.

The present invention provides pharmaceutical compositions containing, as active ingredient, a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament for peroral use, in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents or syrups.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5, usually from 0.5 to 95% especially from 0.5 to 90%, of the active ingredient by weight of the total composition.

In addition to a compound of the invention, the pharmaceutical compositions and medicaments according to the invention can also contain other pharmaceutically active compounds, in particular those active compounds which are customary as combination partners for substances having an influence on the circulation and having a spasmolytic action, such as, for example, saluretic agents, diuretic agents and $\beta$-blockers. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from 0.005 to 500 mg intravenously or from 5 to 250 mg orally of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally, preferably perlingually or intravenously. Preferred pharmaceutical compositions and medicaments are therefore those adapted for perlingual or intravenous administration, such as tablets, pills, dragees or capsules or injection solutions or suspensions or ampoules thereof, respectively. Administration in the method of the invention is preferably perlingually or intravenously.

In general, it has proved advantageous to administer amounts of from 0.0001 to 10 mg/kg, preferably from 0.005 to 5 mg/kg of body weight per day intravenously or from 0.01 to 20 mg/kg preferably from 0.1 to 5 mg/kg of body weight per day orally to achieve effective results. Nevertheless, it can at times be necessary to deviate from those dosage rates, and in particular to do so as a function of the nature and body weight of the warm-blooded animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day.

PREPARATION EXAMPLES

Example 1

1,4-Dihydro-3,6-dimethyl-4-phenyl-pyridazine-5-carboxylic acid methyl ester

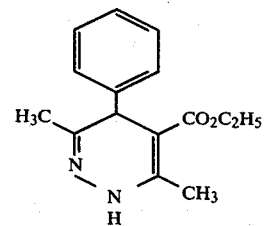

19 g (75 mmols) of 2-acetyl-4-oxo-3-phenyl-pentanoic acid ethyl ester were heated to the boil together with 3.75 g (75 mmols) of hydrazine hydrate in 100 ml of ethanol under nitrogen for 10 hours. The solvent was then distilled off in vacuo and the residue was recrystallised from isopropanol.

Melting point 118° C., yield: 48% of theory.

Example 2

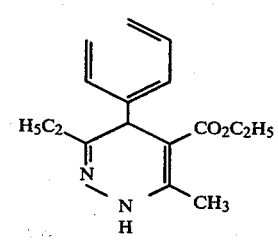

3-ethyl-1,4-dihydro-6-methyl-4-phenyl-pyridazine-5-carboxylic acid ethyl ester of melting point 109° C. (isopropanol) was obtained analogously to Example 1 by reacting 2-acetyl-4-oxo-3-phenyl-hexanoic acid ethyl ester with hydrazine.

Yield: 46% of theory.

EXAMPLE 3

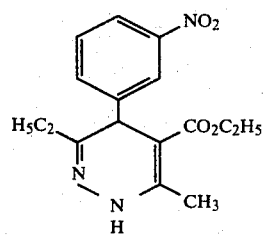

3-ethyl-1,4-dihydro-6-methyl-4-(3'-nitrophenyl)-pyridazine-5-carboxylic acid ethyl ester of melting point 124° C. (isopropanol) was obtained analogously to Example 1 by reacting 2-acetyl-4-oxo-3-(3'-nitrophenyl)-hexanoic acid ethyl ester with hydrazine.

Yield: 21.7% of theory.

EXAMPLE 4

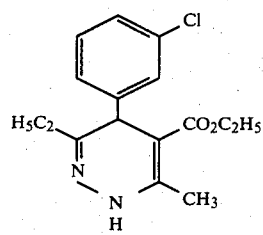

3-ethyl-4-(3'-chlorophenyl)-1,4-dihydro-6-methyl-pyridazine-5-carboxylic acid ethyl ester of melting point 112° C. (isopropanol) was obtained analogously to Example 1 by reacting 2-acetyl-3-(3'-chlorophenyl)-4-oxo-hexanoic acid ethyl ester with hydrazine.

Yield: 50.2% of theory.

Example 5

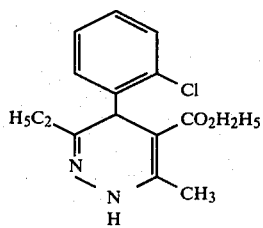

3-ethyl-4-(2'-chlorophenyl)-1,4-dihydro-6-methyl-pyridazine-5-carboxylic acid ethyl ester of melting point 112° C. (isopropanol) was obtained analogously to Example 1 by reacting 2-acetyl-3-(2'-chlorophenyl)-4-oxo-hexanoic acid ethyl ester with hydrazine.

Yield: 48% of theory.

Example 6

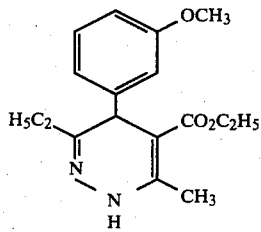

3-ethyl-1,4-dihydro-4-(3'-methoxyphenyl)-6-methyl-pyridazine-5-carboxylic acid ethyl ester of melting point 89° C. (isopropanol) was obtained analogously to Example 1 by reacting 2-acetyl-3-(3'-methoxyphenyl)-4-oxo-hexanoic acid ethyl ester with hydrazine.

Yield: 56% of theory.

Example 7

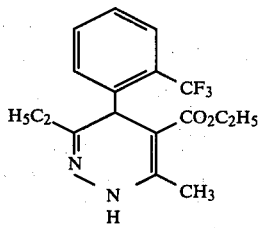

3-ethyl-1,4-dihydro-6-methyl-4-(2'-trifluoromethylphenyl)-pyridazine-5-carboxylic acid ethyl ester of melting point 124° C. (isopropanol) was obtained analogously to Example 1 by reacting 2-acetyl-4-oxo-3-(2'-trifluoromethylphenyl)-hexanoic acid ethyl ester with hydrazine.

Yield: 56% of theory.

Example 8

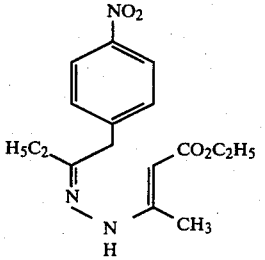

3-ethyl-1,4-dihydro-6-methyl-4-(4'-nitrophenyl)-pyridazine-5-carboxylic acid ethyl ester of melting point 141° C. (isopropanol) was obtained analogously to Example 1 by reacting 2-acetyl-4-oxo-3-(3'-nitrophenyl)-hexanoic acid ethyl ester with hydrazine.

Yield: 62% of theory.

Example 9

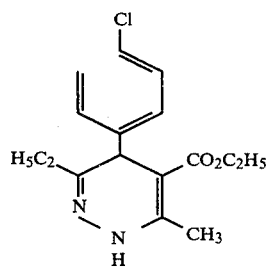

3-ethyl-4-(4'-chlorophenyl)-1,4-dihydro-6-methyl-pyridazine-5-carboxylic acid ethyl ester of melting point 111° C. (isopropanol) was obtained analogously to Example 1 by reacting 2-acetyl-3-(4'-chlorophenyl)-4-oxo-hexanoic acid ethyl ester with hydrazine.

Yield: 39% of theory.

Example 10

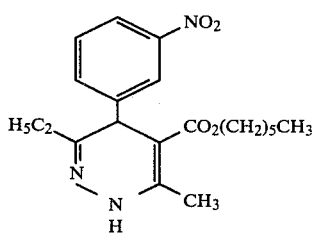

3-ethyl-1,4-dihydro-6-methyl-4-(3'-nitrophenyl)-pyridazine-5-carboxylic acid n-hexyl ester of melting point 92° C. (isopropanol) was obtained analoglously to Example 1 by reacting 2-acetyl-3-(3'-nitrophenyl)-4-oxo-hexanoic acid n-hexyl ester with hydrazine.

Yield: 83% of theory.

Example 11

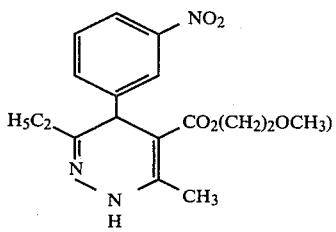

3-ethyl-1,4-dihydro-6-methyl-4-(3'-nitrophenyl)-pyridazine-5-carboxylic acid β-methoxyethyl ester of melting point 141° C. (isopropanol) was obtained analogously to Example 1 by reacting 2-acetyl-3-(3'-nitrophenyl)-4-oxo-hexanoic acid β-methoxyethyl ester with hydrazine.

Yield: 67% of theory.

Example 12

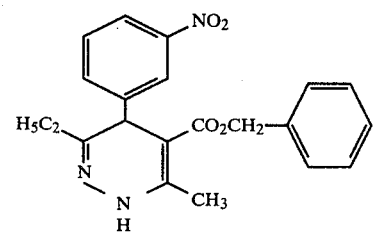

3-ethyl-1,4-dihydro-6-methyl-4-(3'-nitrophenyl)-pyridazine-5-carboxylic acid benzyl ester of melting point 154° C. (isopropanol) was obtained analogously to Example 1 by reacting 2-acetyl-3-(3'-nitrophenyl)-4-oxo-hexanoic acid benzyl ester with hydrazine.

Yield: 43% of theory.

Example 13

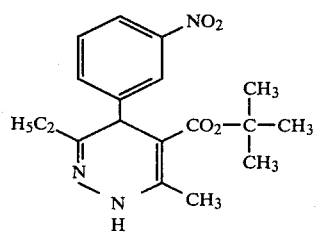

3-ethyl-1,4-dihydro-6-methyl-4-(3'-nitrophenyl)-pyridazine-5-carboxylic acid t-butyl ester of melting point 122° C. (isopropanol) was obtained analogously to Example 1 by reacting 2-acetyl-3-(3'-nitrophenyl)-4-oxo-hexanoic acid t-butyl ester with hydrazine.

Yield: 26% of theory.

Example 14

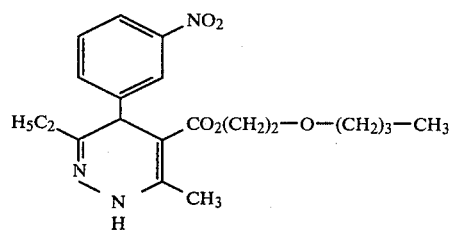

3-ethyl-1,4-dihydro-6-methyl-4-(3'-nitrophenyl)-pyridazine-5-carboxylic acid β-n-butoxyethyl ester of melting point 122° C. (isopropanol) was obtained analogously to Example 1 by reacting 2-acetyl-3-(3'-nitrophenyl)-4-oxo-hexanoic acid β-n-butoxyethyl ester with hydrazine.

Yield: 72% of theory.

Example 15

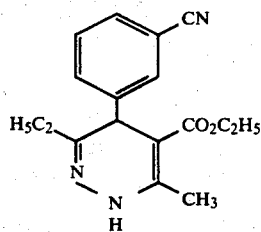

3-ethyl-4-(3'-cyanophenyl)-1,4-dihydro-6-methyl-pyridazine-5-carboxylic acid ethyl ester of melting point 91° C. (isopropanol) was obtained analogously to Example 1 by reacting 2-acetyl-3-(3'-cyanophenyl)-4-oxo-hexanoic acid ethyl ester with hydrazine.

Yield: 38% of theory.

Example 16

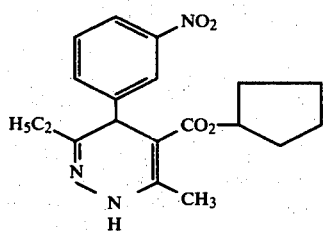

3-ethyl-1,4-dihydro-6-methyl-4-(3'-nitrophenyl)-pyridazine-5-carboxylic acid cyclopentyl ester of melting point 110° C. (isopropanol) was obtained analogously to Example 1 by reacting 2-acetyl-3-(3'-nitrophenyl)-4-oxo-hexanoic acid cyclopentyl ester with hydrazine.

Yield: 68% of theory.

Example 17

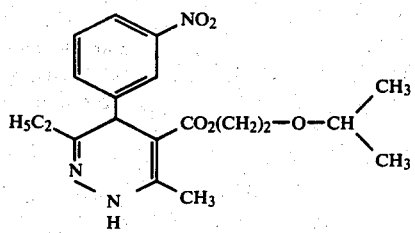

3-ethyl-1,4-dihydro-6-methyl-4-(3'-nitrophenyl)-pyridazine-5-carboxylic acid β-i-propoxyethyl ester of melting point 84° C. (isopropanol) was obtained analogously to Example 1 by reacting 2-acetyl-3-(3'-nitrophenyl)-4-oxo-hexanoic acid β-i-propoxyethyl ester with hydrazine.

Yield: 46% of theory.

Example 18

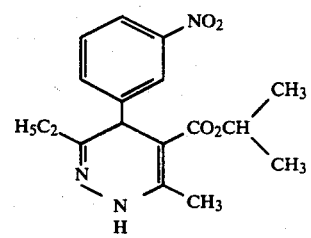

3-ethyl-1,4-dihydro-6-methyl-4-(3'-nitrophenyl)-pyridazine-5-carboxylic acid isopropyl ester of melting point 108° C. (isopropanol) was obtained analogously to Example 1 by reacting 2-acetyl-3-(3'-nitrophenyl)-4-oxo-hexanoic acid isopropyl ester with hydrazine.

Yield: 42% of theory.

Example 19

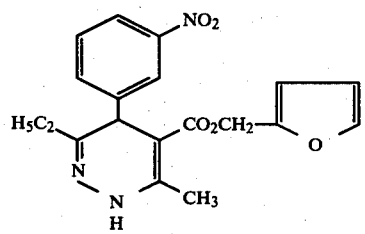

3-ethyl-1,4-dihydro-6-methyl-4-(3'-nitrophenyl)-pyridazine-5-carboxylic acid furfuryl ester of melting point 152° C. (isopropanol) was obtained analogously to Example 1 by reacting 2-acetyl-3-(3'-nitrophenyl)-4-oxo-hexanoic acid furfuryl ester with hydrazine.

Yield: 80% of theory.

Example 20

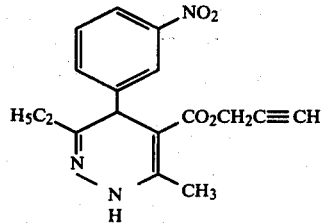

3-ethyl-1,4-dihydro-6-methyl-4-(3'-nitrophenyl)-pyridazine-5-carboxylic acid propargyl ester of melting point 70° C. (isopropanol) was obtained analogously to Example 1 by reacting 2-acetyl-3-(3'-nitrophenyl)-4-oxo-hexanoic acid propargyl ester with hydrazine.

Yield: 29% of theory.

Example 21

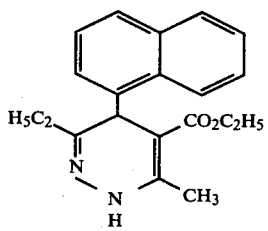

3-ethyl-1,4-dihydro-6-methyl-4-α-naphthyl-pyridazine-5-carboxylic acid ethyl ester of melting point 122° C. (isopropanol) was obtained analogously to Example 1 by reacting 2-acetyl-3-α-naphthyl-4-oxo-hexanoic acid ethyl ester with hydrazine.

Yield: 72% of theory.

Example 22

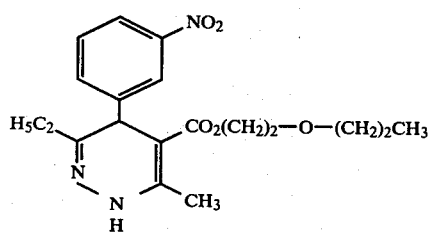

3-ethyl-1,4-dihydro-6-methyl-4-(3'-nitrophenyl)-pyridazine-5-carboxylic acid β-n-propoxyethyl ester of melting point 76° C. (isopropanol) was obtained analogously to Example 1 by reacting 2-acetyl-3-(3'-nitrophenyl)-4-oxo-hexanoic acid β-n-propoxyethyl ester with hydrazine.

Yield: 22% of theory.

Example 23

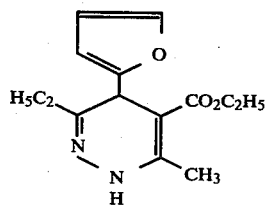

3-ethyl-dihydro-4-(fur-2-yl)-6-methyl-pyridazine-5-carboxylic acid ethyl ester of melting point 82° C. (isopropanol) was obtained analogously to Example 1 by reacting 2-acetyl-4-(fur-2-yl)-4-oxo-hexanoic acid ethyl ester with hydrazine.

Yield: 49% of theory.

Example 24

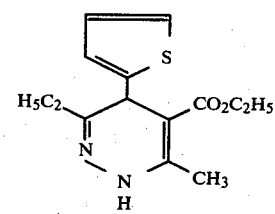

3-ethyl-1,4-dihydro-6-methyl-5-(thien-2-yl)-pyridazine-5-carboxylicacid ethyl ester of melting point 127° C. (isopropanol) was obtained analogously to Example 1 by reacting 2-acetyl-4-oxo-3-(thien-2-yl)-hexanoic acid ethyl ester with hydrazine.

Yield: 61% of theory.

Example 25

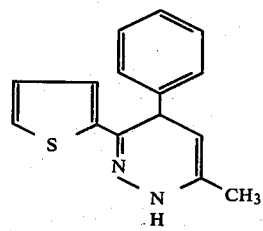

1,4-dihydro-6-methyl-4-phenyl-3-(thien-2-yl)-pyridazine of melting point 150° C. was obtained analogously to Example 1 by reacting 2-phenyl-1-(thien-2-yl)-pentane-1,4-dione with hydrazine.

Yield: 83% of theory.

Example 26

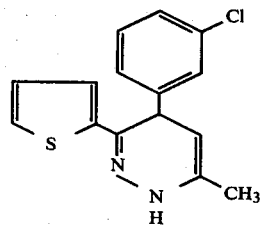

4-(3'-Chlorophenyl)-1,4-dihydro-6-methyl-3-(thien-2-yl)-pyridazine of melting point 109° C. (isopropanol) was obtained analogously to Example 1 by reacting 2-(3'-chlorophenyl)-1-(thien-2-yl)-pentane-1,4-dione with hydrazine.

Yield: 86% of theory.

Example 27

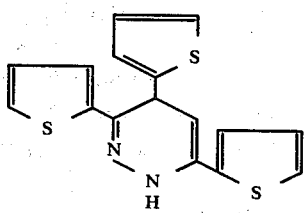

1,4-Dihydro-3,4,6-tri-(thien-2-yl)-pyridazine of melting point 168° C. (isopropanol) was obtained analogously to Example 1 by reacting 1,2,4-tri-(thien-2-yl)-butane-1,4-dione with hydrazine.

Yield: 78% of theory.

Example 28

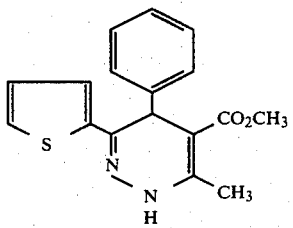

1,4-Dihydro-6-methyl-4-phenyl-3-(thien-2-yl)-pyridazine-5-carboxylic acid methyl ester of melting point 194° C. (isopropanol) was obtained analogously to Example 1 by reacting 2-acetyl-4-oxo-3-phenyl-4-(thien-2-yl)-butyric acid methyl ester with hydrazine.

Yield: 38% of theory.

Example 29

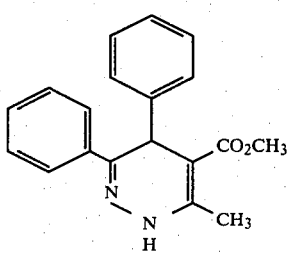

1,4-Dihydro-3,4-diphenyl-6-methyl-pyridazine-5-carboxylic acid methyl ester of melting point 158° C. (isopropanol) was obtained analogously to Example 1 by reacting 2-acetyl-3-benzoyl-3-phenyl-propionic acid methyl ester with hydrazine.

Yield: 24% of theory.

Example 30

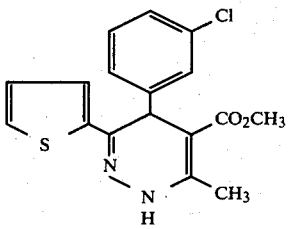

4-(3'-Chlorophenyl)-1,4-dihydro-6-methyl-3-(thien-2-yl)-pyridazine-5-carboxylic acid methyl ester of melting point 191° C. (isopropanol) was obtained analogously to Example 1 by reacting 2-acetyl-3-(3'-chlorophenyl)-4-oxo-4-(thien-2-yl)-butyric acid methyl ester with hydrazine.

Yield: 18% of theory.

Example 31

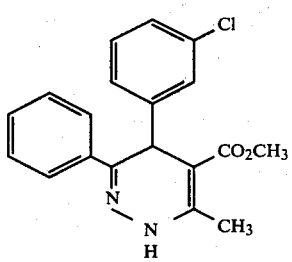

4-(3'-Chlorophenyl)-1,4-dihydro-6-methyl-3-phenyl-pyridazine-5-carboxylic acid methyl ester of melting point 189° C. (isopropanol) was obtained analogously to Example 1 by reacting 2-acetyl-3-benzoyl-3-phenylpropionic acid methyl ester with hydrazine.

Yield: 15.7% of theory.

Example 32

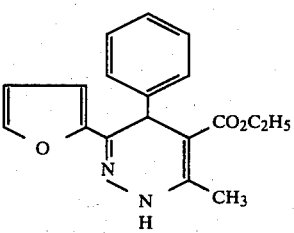

1,4-Dihydro-3-(fur-2-yl)-6-methyl-4-phenyl-pyridazine-5-carboxylic acid ethyl ester of melting point 158° C. (isopropanol) was obtained analogously to Example 1 by reacting 2-acetyl-4-(fur-2-yl)-4-oxo-3-phenyl-butyric acid ethyl ester with hydrazine.

Yield: 48% of theory.

Example 33

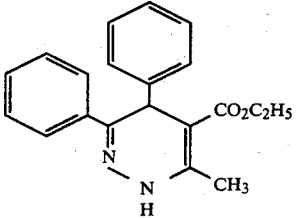

1,4-Dihydro-3,4-diphenyl-6-methyl-pyridazine-5-carboxylic acid ethyl ester of melting point 130° C. was obtained analogously to Example 1 by reacting 2-acetyl-3-benzoyl-3-phenyl-propionic acid ethyl ester with hydrazine.

Yield: 18% of theory.

Example 34

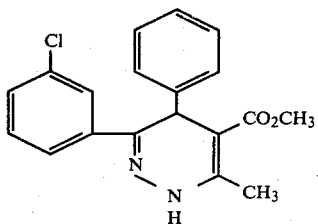

3-(3'-Chlorophenyl)-1,4-dihydro-6-methyl-4-phenyl-pyridazine-5-carboxylic acid methyl ester of melting point 176° C. (isopropanol) was obtained analogously to Example 1 by reacting 2-acetyl-3-(3'-chlorobenzoyl)-3-phenyl-propionic acid methyl ester with hydrazine.

Yield: 26% of theory.

Example 35

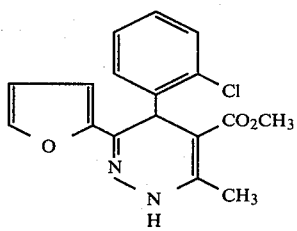

4-(2'-Chlorophenyl)-1,4-dihydro-3-(fur-2-yl)-6-methyl-pyridazine-5-carboxylic acid methyl ester of melting point 195° C. (isopropanol) was obtained analogously to Example 1 by reacting 2-acetyl-3-(2'-chlorophenyl)-4-(fur-2-yl)-4-oxo-butyric acid methyl ester with hydrazine.

Yield: 24% of theory.

Example 36

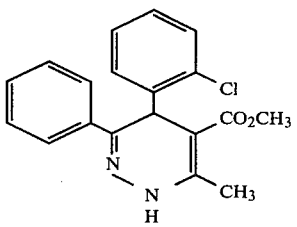

4-(2'-Chlorophenyl)-1,4-dihydro-6-methyl-3-phenyl-pyridazine-5-carboxylic acid methyl ester of melting point 198° C. (isopropanol) was obtained analogously to Example 1 by reacting 2-acetyl-3-benzoyl-3-(2'-chlorophenyl)-propionic acid methyl ester with hydrazine.

Yield: 18.9% of theory.

EXAMPLE 37

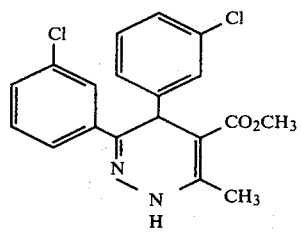

3,4-Di-(3'-chlorophenyl)-1,4-dihydro-6-methyl-pyridazine-5-carboxylic acid methyl ester of melting point 204° C. (isopropanol) was obtained analogously to Example 1 by reacting 2-acetyl-3-(3'-chlorobenzoyl)-3-(3'-chlorophenyl)-propionic acid methyl ester with hydrazine.

Yield: 12.4% of theory.

EXAMPLE 38

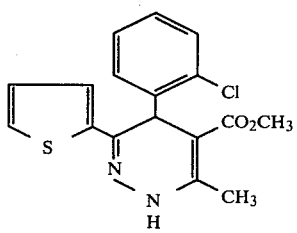

4-(2'-Chlorophenyl)-1,4-dihydro-6-methyl-3-(thien-2-yl)-pyridazine-5-carboxylic acid of melting point 188° C. (isopropanol) was obtained analogously to Example 1 by reacting 2-acetyl-3-(2'-chlorophenyl)-4-oxo-4-(thien-2-yl)-butyric acid methyl ester with hydrazine.

Yield: 18.3% of theory.

EXAMPLE 39

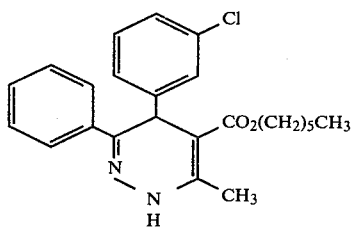

4-(3'-Chlorophenyl)-1,4-dihydro-6-methyl-3-phenyl-pyridazine-5-carboxylic acid n-hexyl ester of melting point 103° C. (isopropanol) was obtained analogously to Example 1 by reacting 2-acetyl-3-benzoyl-3-(3'-chlorophenyl)-propionic acid n-hexyl ester with hydrazine.

Yield: 45.1% of theory.

EXAMPLE 40

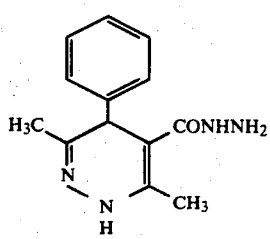

1,4-Dihydro-3,6-dimethyl-4-phenyl-pyridazine-5-carboxylic acid hydrazide of melting point 156° (ethanol) was obtained analogously to Example 1 by reacting 2-acetyl-4-oxo-3-phenyl-pentanecarboxylic acid hydrazide with hydrazine.

Yield: 32% of theory.

EXAMPLE 41

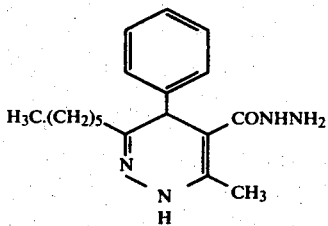

1,4-Dihydro-6-methyl-3-n-pentyl-4-phenyl-pyridazine-5-carboxylic acid hydrazide of melting point 161° (ethanol) was obtained analogously to Example 1 by reacting 2-acetyl-4-oxo-3-phenyl-decanecarboxylic acid hydrazide with hydrazine.

Yield: 29% of theory.

EXAMPLE 42

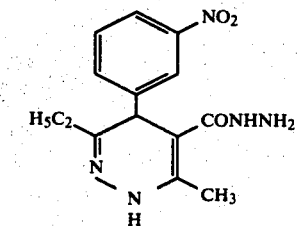

3-ethyl-1,4-dihydro-6-methyl-4-(3'-nitrophenyl)-pyridazine-5-carboxylic acid hydrazide of melting point 98° (ethanol) was obtained analogously to Example 1 by reacting 2-acetyl-4-oxo-3-(3'-nitrophenyl)-hexanoic acid hydrazide with hydrazine.

Yield: 28% of theory.

What is claimed is:

1. A compound of the formula I

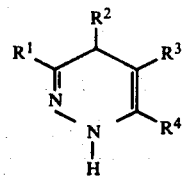

wherein $R^1$ is a straight or branched alkyl radical with up to 6 carbon atoms optionally substituted by one substituent selected from fluoro, chloro or phenyl; or represents thienyl, furyl or phenyl, the phenyl optionally having 1 substituent from the group halogen, nitro, cyano, of hydroxyl, $R^2$ represents phenyl, naphthyl, thienyl or furyl, the above mentioned phenyl optionally having 1 or 2 identical or different substituents selected from the group alkyl with 1 to 2 carbon atoms, alkoxy with 1 to 2 carbon atoms or halogen, or substituted by one of cyano, nitro, hydroxyl, trifluoromethyl or trifluoromethoxy;

$R^3$ is hydrogen or the group $COOR^6$, wherein $R^6$ is a straight-chain branched saturated or unsaturated aliphatic hydrocarbon radical having up to 6 carbon atoms, which is optionally interrupted in the chain by 1 oxygen atom and/or which is optionally substituted by hydroxyl, halogen, phenyl or phenoxy; or is cyclopentyl or cyclohexyl and $R^4$ is alkyl with 1 to 4 carbon atoms, or fluoroalkyl with 1 or 2 carbon atoms, phenyl optionally substituted by nitro, or is thienyl or furyl.

2. A compound of claim 1 wherein $R^1$ is alkyl having up to 6 carbon atoms; phenyl; phenyl substituted by halogen; furyl or thienyl; $R^2$ is phenyl; naphthyl; phenyl substituted by halogen, nitro, alkoxy having 1 to 4 carbon atoms, trifluoromethyl or cyano; furyl or thienyl; $R^3$ represents hydrogen or a group $COOR^6$ wherein $R^6$ is straight or branched alkyl, alkenyl or alkinyl having up to 6 carbon atoms, alkoxyalkyl having 1 to 4 carbon atoms in each alkyl moiety, alkyl having up to 6 carbon atoms substituted by phenyl, or cycloalkyl of 5 to 6 carbon atoms.

3. A compound of claim 1 which is 3-ethyl-1,4-dihydro-6-methyl-4-(3'-nitrophenyl)-pyridazine-5-carboxylic acid β-methoxyethyl ester.

4. A pharmaceutical composition containing as an active ingredient a cononary dilating effective amount of a compound according to claim 1 in admixture with a solid or liquefied gaseous diluent or in admixture with a liquid diluent other than a solvent of a molecular weight less than 200 except in the presence of a surface-active agent.

5. A pharmaceutical composition containing as an active ingredient a cononary-dilating effective amount of a compound according to claim 1 in the form of a sterile or physiologically isotonic aqueous solution.

6. A composition according to claim 4 containing from 0.5 to 90% by weight of the said active ingredient.

7. A medicament in dosage unit form comprising an effective amount of a coronary-dilating effective amount of a compound according to claim 1 in an inert pharmaceutical carrier.

8. A medicament of claim 7 in the form of tablets, pills, dragees, capsules, ampoules, or suppositories.

9. A method of combating circulatory diseases in warm-blooded animals which comprises administering to the animals a cononary-dilating effective amount of an active compound according to claim 1 either alone or in admixture with a diluent or in the form of a medicament according to claim 7.

10. A method according to claim 9 in which the active compound is administered in an amount of 0.0001 to 10 mg per kg body weight per day intravenously.

11. A method according to claim 9 in which the active compound is administered in an amount of 0.01 to 20 mg per kg body weight per day orally.

12. A method according to claim 10 or 11 in which the animals are ruminants.

13. A method according to claim 9 in which the active compound is administered orally.

* * * * *